(12) United States Patent
Holländer et al.

(10) Patent No.: US 10,514,330 B2
(45) Date of Patent: Dec. 24, 2019

(54) DEVICE FOR ISOLATION AND/OR PURIFICATION OF BIOMOLECULES

(75) Inventors: Vera Holländer, Unna (DE); Markus Müller, Dormagen (DE); Karin Schulte, Düsseldorf (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/809,563

(22) PCT Filed: Jul. 13, 2011

(86) PCT No.: PCT/EP2011/061954
§ 371 (c)(1),
(2), (4) Date: Jan. 10, 2013

(87) PCT Pub. No.: WO2012/007502
PCT Pub. Date: Jan. 19, 2012

(65) Prior Publication Data
US 2013/0115693 A1    May 9, 2013

(30) Foreign Application Priority Data
Jul. 14, 2010  (EP) ..................................... 10007275

(51) Int. Cl.
*G01N 1/40*          (2006.01)
(52) U.S. Cl.
CPC ................... *G01N 1/4005* (2013.01)
(58) Field of Classification Search
CPC ...... A61M 1/36; A61M 1/3618; A61M 1/362; A61M 1/3693; B01D 21/262; B01D 2221/10; B01L 3/5021; B01L 3/5082; B01L 2200/0631; B01L 2300/042; B01L 2300/0681; B01L 2300/0832; B01L 2300/0858; B01L 2300/0877; B01L 3/50
See application file for complete search history.

(56) References Cited

U.S. PATENT DOCUMENTS

| | | | | |
|---|---|---|---|---|
| 4,244,694 A * | 1/1981 | Farina et al. | .................. | 436/500 |
| 4,486,315 A * | 12/1984 | Teipel | ................ | B01D 11/0288 |
| | | | | 210/518 |
| 4,515,889 A * | 5/1985 | Klose | ....................... | B01F 5/064 |
| | | | | 422/548 |
| 4,787,971 A | 11/1988 | Donald | | |
| 5,114,858 A * | 5/1992 | Williams | ............... | C12M 47/06 |
| | | | | 422/527 |
| 5,354,483 A * | 10/1994 | Furse | ........................... | 210/789 |
| 5,364,533 A | 11/1994 | Ogura et al. | | |
| 5,552,325 A * | 9/1996 | Nochumson et al. | ........ | 436/177 |
| 6,251,660 B1 | 6/2001 | Muir et al. | | |
| 6,582,665 B2 | 6/2003 | Faulkner | | |
| 2002/0096469 A1 | 7/2002 | Faulkner | | |
| 2002/0110495 A1* | 8/2002 | Hunt et al. | .................... | 422/101 |
| 2005/0191760 A1* | 9/2005 | Heath et al. | .................. | 436/177 |
| 2006/0180548 A1 | 8/2006 | Ji | | |
| 2007/0292858 A1* | 12/2007 | Chen | ...................... | B01L 3/502 |
| | | | | 435/6.18 |
| 2008/0190830 A1* | 8/2008 | Maltezos | ............. | G01N 30/603 |
| | | | | 210/198.2 |
| 2008/0300397 A1 | 12/2008 | Kenrick et al. | | |
| 2010/0120129 A1* | 5/2010 | Amshey | ............ | B01L 3/502715 |
| | | | | 435/270 |
| 2011/0146418 A1 | 6/2011 | Brevnov et al. | | |

FOREIGN PATENT DOCUMENTS

| | | |
|---|---|---|
| DE | 2 125 027 A1 | 12/1971 |
| EP | 0 268 946 A2 | 6/1988 |
| EP | 1 990 641 A1 | 11/2008 |
| WO | 01/94574 A2 | 12/2001 |
| WO | 2005/068610 A1 | 7/2005 |
| WO | 2008/150779 A1 | 12/2008 |
| WO | 2009/157435 A1 | 12/2009 |

OTHER PUBLICATIONS

Siddappa et al. Regeneration of Commercial Nucleic Acid Extraction Columns Without the Risk of Carryover Contamination. BioTechniques, 2007. 42:186-192.*
"Planned Obsolescence". The Economist, 2009, pp. 1-3, downloaded from http://www.economist.com/node/13354332/print on Dec. 14, 2015.*

* cited by examiner

*Primary Examiner* — Christopher M Babic
*Assistant Examiner* — Kimberly A. Aron
(74) *Attorney, Agent, or Firm* — Seed IP Law Group LLP

(57) ABSTRACT

The present invention refers to a device, comprising a hollow body having at least one open end comprising at least one solid matrix binding, adsorbing, absorbing, chelating or retaining compounds which are not desired in a sample and preferably at least one barrier which is non-permeable for liquids and solids under ambience conditions, however, becomes liquid-permeable by applying an external force to the barrier, the use of such a device for isolating or purifying a biomolecule from a sample, a method for preparation of the device and a method for isolation or purification of any biomolecule using said device.

22 Claims, 2 Drawing Sheets

DEVICE FOR ISOLATION AND/OR PURIFICATION OF BIOMOLECULES

The present invention refers to a device, comprising a hollow body having at least one open end comprising at least one solid matrix binding, adsorbing, absorbing, chelating or retaining compounds which are not desired in a sample, the use of such a device for isolating or purifying a biomolecule from a sample, a method for preparation of said device and a method for isolation or purification of any biomolecule using said device.

During the treatment of biological samples, e.g. for isolating or purifying biomolecules from said samples, it is very common that the sample is contacted with any binding, absorbing, adsorbing, chelating or filtering matrix, wherein commonly the interesting compounds are bound, adsorbed or absorbed by said matrix or the sample is chromatographically separated according to the size of the compounds contained therein, thereby the interesting compounds are separated from any remainder. Several well-known approaches for biomolecule isolation are described in the state of the art, encompassing the binding of biomolecules to any matrix, like e.g. DNA or RNA binding to columns of nucleic acid binding materials, affinity binding, e.g. of proteins or low molecular molecules, or chromatographic devices separating the biomolecules according to their size or volume. Usually all these procedures comprise several washing and elution steps, and optionally a monitoring of the elution is necessary, accordingly several method steps have to be carried out before the interesting biomolecule is obtained in desired form. Therefore such types of methods are laborious, susceptible for contaminations and time-consuming.

Another approach is binding, absorbing, adsorbing or chelating undesired compounds of a sample to separate them from the desired biomolecules, like e.g. using Chelex 100 for DNA isolation as described in Walsh et. Al, BioTechniques Vol. 10, No 4 (1991) or Burkhart et al 2002, J Biochem Biophys Methods 52 (2002) 145-149. Such a separation of the undesired compounds usually is carried out as a batch procedure, wherein the sample is contacted with the binding, absorbing, adsorbing or chelating matrix, incubated and thereafter the solid material is separated from the sample, e.g. by centrifugation. The supernatant comprising the interesting compound is then removed, e.g. by pipetting. Said remove has to be carried out very careful not to risk any contamination by the solid matrix, but to obtain as much of the supernatant as possible. In such an approach again several method steps have to be carried out which makes the methods laborious, susceptible for contaminations and time-consuming.

The object of the present invention was to provide a method and a device allowing a simple and effective separation of contaminating compound(s) interfering with later biomolecule processing steps from any interesting biomolecule with less pipetting steps and diminished risk for cross-contamination. Further the device should allow automatisation of the procedure.

This object is met by providing a device comprising (i) at least one hollow body (1), each hollow body (1) having at least one open end; (ii) at least one type of solid or gelly material binding, adsorbing, absorbing, chelating or retaining compounds contaminating any desired biomolecule; (iii) optionally at least one porous liquid-permeable element (4) inside of the hollow body; (iv) optionally at least one removable closing device (6) to seal at least one of the open ends.

The device further comprises preferably at least one barrier (5) which is non-permeable for liquids and solids under ambience conditions, however, becomes liquid-permeable by applying an external force to said barrier (5)

Said device can be used for treating any liquid comprising sample, e.g. a liquid sample comprising a biomolecule of interest and/or for isolating or purifying a biomolecule of interest from such a sample.

Figure 1:
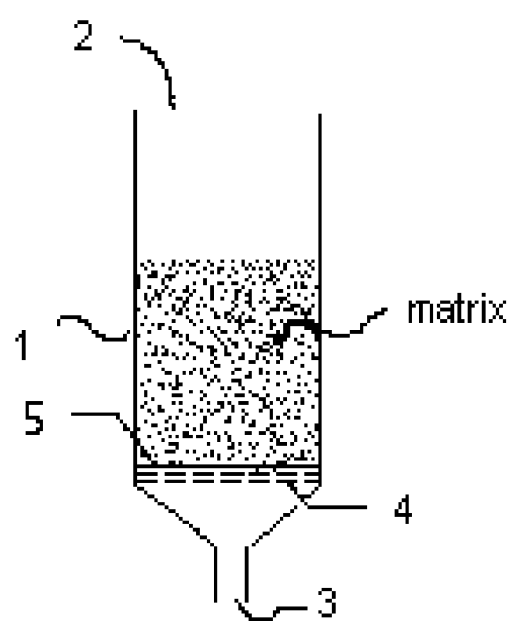
FIG. 1 shows one embodiment of the device of the present invention, which is a spin column comprising a hollow body (1), an inlet (2) and an outlet (3), a porous frit (4), a polystyrene film or aluminium foil as a barrier (5) and Chelex resin (matrix).
Figure 2:
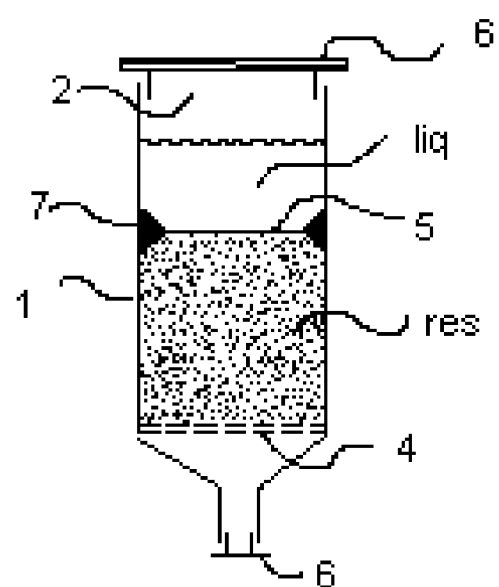
FIG. 2 shows one embodiment of the device of the present invention, which is a spin column comprising a hollow body (1), an inlet (2) and an outlet (3), a porous frit (4), a polystyrene film (5), a holder (7) and two removable closing devices (6), further comprising a particulate ion exchanging material (matrix) and a buffer (liq.).

The hollow body (1) of the device disclosed herein can be made of any material suitable for sample collection, storage or treatment, like plastic, metal, glass, porcelain or similar, preferably the body is made of plastic. In particular the body preferably is made of a thermosetting or thermoplastic resin like polypropylene, polyethylene, polypropylene-copolymers, polyvinylchloride, polyurethane, polycarbonate, polyamide, polyimide, polystyrene, polyethyleneterephthalate, polylactide, ethylene-polyvinylacetate, vinylchloride vinylacetate copolymers, polyacetales, polyetheralcohols, vinylacetate copolymers or arylic polymers without being restricted to these.

The hollow body/each of the hollow bodies of the device has at least one open end, which means that at least one end allows to insert something into the hollow body, like e.g. to insert the sample of interest and/or any liquid, or to remove something from the hollow body. Preferably the device has an inlet (2) and an outlet (3), wherein typically the inlet opening is on the "upper" end of the device and the outlet opening is on the "bottom" side of the device. Particularly preferred the inlet (2) and the outlet (3) are opposed to each other. Optionally the device further comprise at least one removable closing device (6), which closes removably at least one of the openings, e.g. the outlet (3) or the inlet (2), or several (optionally differently shaped) closing devices for all the openings.

A biomolecule according to the present invention is any molecule occurring in a biological sample. A biological sample can be any body fluid or tissue or a human or animal including insects, like blood, plasma, serum, blood fractions like leukocyte fraction or buffy coat, urine, serum, liquor, sputum, sperm, saliva etc, tissue of any organ, brain, skin, muscle etc.; scales; swabs; faeces; keratinic samples like hair, nails, horns or antlers; carapaces or wings (in particular of insects); cell suspensions or cell cultures, cell fragments or cell organelles like chloroplasts or mitochondrions, vesicles, nuclei or chromosomes; samples comprising bacterial, fungal or yeast cells or fragments, any type of virus, viroid or prions; histological samples like punctates or tissue slices; tissue cultures; plants; plant parts, cells or tissue; samples taken from the environment, like e.g. water, dust, air or mud samples; food samples; forensic samples like cigarette filters, textile samples, tooth brush; any solution comprising an prepurified or preisolated biomolecule etc. without being restricted to the mentioned examples.

Accordingly a biomolecule is any nucleic acid like DNA or RNA, in particular lienar, branched or circular, single stranded or double stranded nucleic acids, more particular mRNA, sRNA, miRNA, snRAN, tRNA, hnRNA or ribozymes, genomic, plasmid or organelles DNA; any nucleotide, oligonucleotide or polynucleotide, even synthetic, modified or labeled oligo- or polynucleotides; PCR-primers, short DNA or RNA fragments for hybridization; PNAs (peptide nucleic acids); any protein, peptide or amino acid, including unlabeled or labeled antibodies, receptors, hormones, growth factors and modified proteins, nucleic acids, proteins and peptides of infectious origin; metabolite, any lipid; sugar (monomer, oligomer or polymer); proteoglucanes; any low molecular pathway product, signal molecule, receptor or enzyme activator or inhibitor; agents, medicaments and metabolites of medicaments, medicaments or any other biomolecule of interest.

The compounds considered as contaminants are such compounds which are not desired in the particulate approach. For instance if one type of biomolecule is of interest, e.g. nucleic acids shall be isolated, all the other types of biomolecules as well as any further compounds for this approach can be considered as contaminants. In particular such compounds can be considered as contaminants which are interfering with any later treatment or detection of the biomolecule of interest. Examples for contaminants are melanin, eumelanin, hemoglobin, immunoglobin, myoglobin, proteinases, humic acid or derivatives, metallic ions, urea, colorants or dyes, polysaccharides, secondary plant metabolites, endotoxins, bile acid, tannic agents, beside the other biomolecules cited above which for the according approach might be undesired.

According to the invention inside of the hollow body (1) the device has at least one type of a solid or gelly matrix binding, absorbing, adsorbing, chelating or retaining undesired compounds contaminating the desired biomolecule(s). For example the device may comprise a binding, absorbing, adsorbing or chelating matrix for specific or unspecific binding, absorption, adsorption or chelating of sample compositions, a filtration material retaining contaminants, beads for lysis of cells or for binding of cell components, or any other component commonly used for biomolecule isolation or purification as far as they are retaining contaminants, but not the biomolecules of interest. It is particularly preferred that the matrix is a particulate solid material which adsorbes, absorbes, chelates or binds undesired compounds of the biological sample, whereas the biomolecule(s) of interest is/are essentially not adsorbed, absorbed or bound. One preferred solid particulate matrix comprises or consists of a chelating resin purifying compounds by ion exchange, chelating e.g. metal ions, in particular transition metal ions. Such a commonly known resin is a styrene-divinylbenzene resin comprising imino diacetic acid groups, sold under the name Chelex 100 (Biorad), which is suitably used for DNA or RNA isolation, wherein the nucleic acids don't bind to said resin. Further any inert material like e.g. agarose, Sephacryl resin, silicone; latex; polysaccharides, cellulose ether and derivatives, thermosetting of thermoplastic polymers, metals or further solid matrices like beads, films, foils, particles etc. may be used. Said materials may comprise functional groups on their surface(s) selectively binding any of the undesired contaminants. A further preferred matrix comprises or consists of a ion exchanging matrix or a matrix comprising specific binding sites for biological compounds. The matrix further may comprise woven or non-woven fibers or a fleece, e.g. of silica, polysaccharides or any other suitable material.

The matrix suitable to separate the contaminants from the desired biomolecules further can comprise or consist of HIC particles (hydrophobic interaction chromatography particles, Dionex Corp., USA), cationic or anionic exchanging material; size exclusion material like agarose; gel filtration material; minerals, like e.g. hydroxylapatit, bentonite, zeolithe, kaolinit, diatomite or processed minerals like silica; InhibitEX® (Qiagen, Hilden, Germany), IDA (iminodiacetic acid), NTA (nitrilo acetic acid), and derivatives of the last two mentioned, a resin or other substrate with IDA or NTA groups or derivates of them, EDTA, specific antibodies, amphipol; charcoal, PVP (polyvinylpyrrolidone); superabsorbing polymers; Non-fat milk cocktails, termed BLOTTO (Bovine Lacto Transfer Technique Optimizer) (in S. H. De Boer*(1995) Nucleic Acids Research, 1995, Vol. 23, No. 13 2567-2568); Polysaccharides, e.g. chitosane, starch, glycogen, cellulose or derivates of them; proteins like specific antibodies or enzymes; without being restricted to the mentioned examples.

All the cited matrix materials can (independently) be present inside of the hollow body (1) in form of e.g. a powder, particles, beads, granules, spheres, a fleece, (a) membrane(s), filter or any other suitable form coming in contact with the biological sample. Furthermore a reversed phase chromatography suitable material may be used.

The hollow body (1) of the device of the present invention can comprise several compartments, e.g. said hollow body (1) is compartmented by at least one liquid permeable element (4) or a barrier (5) which is non-permeable for liquids and solids under ambience conditions, however, becomes liquid-permeable by applying an external force to said barrier (5) which has contact with all of the inner side walls of the hollow body (1) and flushes with said side walls, or is/are placed in a holder (7) which flushes with the side walls. Any remaining gap between the liquid permeable element (4), the barrier (5) or the holder (7) can be sealed with a suitable sealing material.

Preferably the device comprises further at least one liquid permeable element (4) and at least one barrier (5) which is non-permeable for liquids and solids under ambience conditions, however, becomes liquid-permeable by applying an external force to said barrier (5).

The hollow body (1) may comprise at least one type of the solid or gelly matrices cited above which means that it either comprises one selected type of matrix of the matrices cited above or a mixture of matrices in one compartment or it may comprise more than one of said matrices, independently selected from the matrix materials cited above in several compartments inside of the hollow body (1).

Preferably any compartment containing a solid matrix is bordered by at least one liquid permeable element (4), retaining the solid matrix within the compartment independent from any liquid transfer into any further compartment(s) or to the outlet (3) of the device. In a preferred embodiment of the present invention the hollow body (1) of the device comprises inside at least one liquid-permeable element (4) like preferably a porous frit, a filter, a fleece, a fiber matrix or a membrane. Said liquid-permeable element(s) (4) mainly has/have the function to retain any solid material contained in at least one of the hollow body compartments from elution, but to allow any liquid and solved ingredients to pass the element (4). Accordingly e.g. a liquid sample part can be separated from any solid sample part or a liquid sample can be purified by a chromatographic, a filtering, a chelating or a binding matrix contained and retained in the device. Said liquid permeable element(s) (4) preferably is/are in contact with all of the inner side walls of the hollow body (1) and flushes with said side walls, or is/are placed in holder (7) which flushes with the side walls and/or any remaining gap between the liquid permeable element (4) or the holder (7) may be sealed with a suitable sealing material.

If the device comprises several compartments, e.g. two, three or four, it is preferred that at least one of them is filled with at least one type of the binding, absorbing, adsorbing or chelating matrices as cited above, whereas at least one of the other compartments is filled with any further type of a binding, absorbing, adsorbing or chelating matrix, preferably selected from them cited above or with any liquid or solution. Furthermore any compartment of the hollow body (1) can comprise a mixture of any of the solid or gelly matrices cited above and a liquid or solution, e.g. the hollow body comprises a matrix suspended or dispersed in any liquid or solution.

The liquid or solution can be any aqueous or organic based liquid or solution like water, any aqueous buffer, a cell culture medium, a nutrient solution, an organic solvent or any reaction solution or mixtures thereof. Preferably the solution is an aqueous buffer, wherein the buffer is not restricted to a particular buffer, but is preferably any of the buffers commonly used for cell treatment, in particular used during a biomolecule isolation method, or the solution is a cell culture medium or nutrient solution.

In particular if the hollow body (1) of the device comprises or is intended to be used with a liquid, buffer or a solution the hollow body (1) further may comprise at least one barrier (5) which is non-permeable for liquids and solids under ambience conditions, however, becomes liquid-permeable by applying an external force to said barrier (5), wherein said liquid, solution or buffer is prevented from leakage by said at least one barrier (5), which means that either the liquid, solution or buffer is between two barriers (5) or the liquid is retained by one barrier (5) and the device comprises at least one closing device (6). The device further can contain several independently selected liquids in several compartments.

Such a barrier (5) preferably is consisting of a material which is non-permeable for liquids and solids under ambience conditions, however, becomes liquid-permeable by applying an external force to the material, preferably pressure, drag force or driving power. Said at least one barrier (5) is/are in contact with all of the inner side walls of the hollow body (1) and flushes with said side walls, or is/are placed in a holder (7) which flushes with the side walls. Any remaining gap between the barrier (5) or the holder (7) can be sealed with a suitable sealing material. Such a barrier (5) as well may divide the hollow body (1) into at least two compartments.

With "ambience conditions" according to the present application is meant that the barrier material is under the same conditions as the ambience of the device, in particular no external forces are applied to the barrier material. External forces may be increased pressure on at least one of the surfaces or on any of the sides of the barrier, drag forces like vacuum or suction, driving forces like centrifugal forces, shaking or dashing, the last two mentioned preferably by utilization of inertia of the mass, or mechanical forces like puncturing, cutting, rupturing or similar. Accordingly the material is under "ambience conditions" during common handling of the device like standing on the table, pipetting steps, incubation steps or similar. "Increased pressure" means that at least twice the ambient pressure is externally applied to the barrier material. "Increased pressure" does not comprise the slightly increased pressure resulting from any liquid or solid matrix applied to the barrier material, e.g. if a column like a spin column is filled with a liquid or a solid matrix.

With "non-permeable for liquids" is meant that a liquid, e.g. an aqueous solution or water, an alcohol or an organic solution, particularly preferred an aqueous solution, is retained on the surface of the barrier and is not able to pass said barrier under ambience conditions and preferably is not even able to enter, to penetrate or to soak into the barrier material. It is particularly preferred that independent from the time period of contact of the liquid with the barrier said solution cannot pass the barrier as long as no external force is applied.

By applying any of the external forces cited above the material of the barrier (5) becomes liquid-permeable. This means that the material diminishes its barrier character and allows at least any liquid, preferably a solution comprising solved materials, to pass the material. The permeability might be reversible or irreversible after return to ambience conditions. Preferably the permeability is irreversible. Exemplified is this by that the barrier material becomes porous by applying pressure, drag force or driving power, or the barrier material has a predetermined orifice which is closed under ambient conditions, but opens by applying pressure, drag force or driving power. Preferably after porosity is obtained or the orifice opened the barrier remains liquid permeable due to the contained openings, even under ambience conditions. Further the barrier (5) may break, preferably at a predetermined breaking point by applying pressure, drag force or driving power.

A further possibility is that the device comprises inside of the hollow body (1) above or below of the barrier (5) any material or component which punctures, cuts or ruptures the barrier material when an external force like e.g. pressure, drag force or driving power is applied to the device. If the barrier material is punctured, it is preferred that puncturing is micropuncturing, which means that only very small punctures are obtained in the barrier material, not resulting in a rupture of the barrier (5), but making the barrier (5) porous.

With "above" is meant that, if the device is positioned in its use mode, e.g. a column is placed upright in a holder or a cup, the material or component which punctures, cuts or ruptures the barrier material is on the upper side of said barrier material. In particular, if the device is used as intended including any liquid, the the material or component which punctures, cuts or ruptures the barrier material is on the same side as the liquid and is pressed by application of the external force, in particular by applying pressure, drag force or driving power, to the upper surface of the barrier material which as well is in contact with the liquid.

If the material or component which punctures, cuts or ruptures the barrier material is "below" the barrier material the bottom surface of the barrier material will be pressed by the external force to the the material or component which punctures, cuts or ruptures the barrier material. In the latter case the material or component which punctures, cuts or ruptures the barrier material is on the opposite side of the liquid-permeable element (4) as the liquid.

The intensity and type of the applied external force suitable for rendering the barrier(s) (5) liquid permeable depends from the material used for the barrier(s) (5) and optionally from the component or material used for puncturing, cutting or rupturing the barrier(s) (5). It is preferred that the barrier(s) (5) is/are resistant against any external force up to a predetermined intensity, wherein due to the selected material and due to any treatment of the material the intensity when the barrier(s) (5) become(s) liquid permeable varies. For a skilled person it is easy to determine by standard experiments which type of external force and which intensity of any of the forces results in a liquid permeability of the selected materials for the barrier(s) (5). There can be different materials or thickness of the barrier material or a different principle, which results in different intensities of the external force necessary to make the barrier liquid permeable. However, it is particularly preferred that the barrier(s) (5) in any case is/are resistant to 1×g, preferably to 2×g, more preferred to 5×g, even more preferred to 10×g and particularly preferred to 20×g, 40×g or 50×g. It is particularly preferred that the barrier(s) is 7 are resistant to 100×g. In particular the barrier(s) should be resistant against the forces occurring during pipetting, turning, smooth vortexing and other commonly used process steps.

The barrier(s) (5) is/are preferably provided in form of a film, foil, coating, septum, membrane, hydrophobic sintered material (hydrophobic frit), a material which was made hydrophobic by chemical or other treatment or any other suitable form serving as an effective barrier. Suitable materials for the barrier (5) are for example hydrophobic filter materials; hydrophobic fiber web materials; membranes, films or foils of plastics, in particular thermoplastic or thermosetting polymers like polyethylene, polypropylene, polypropylene-copolymers, polyvinylchloride, polyurethane, polycarbonate, polyamide, polyimide, polystyrene, polyethyleneterephthalate, polylactide, ethylene-polyvinylacetate, vinylchloride vinylacetate copolymers, polyacetales, polyetheralcohols, vinylacetate copolymers, arylic polymers; or silicone; latex; polysaccharides, in particular cellulose ether and derivatives; thin metal layers like aluminium foil or copper foil, or any other suitable, preferably film-forming material which can be provided as a film, foil, coating, septum or membrane. As films or coatings thermoplastic polymers like polyethylene, polypropylene, polypropylene-copolymers, polystyrene, polyvinylchloride, polyurethane, polycarbonate or polyamide are particularly preferred. As a hydrophobic filter material a hydrophobized polyethylene filter is preferred, as a membrane a hydrophobized fiber membrane like e.g. any of the Filtrona® fiber membranes (Filtrona, Reinbek, Germany) and as a membrane such a material like Gore Tex® or similar is preferred. Any water-resistant but vapour permeable membrane as well is preferred.

Examples for the component or material which punctures, cuts or ruptures the barrier material are: any solid porous, holey or perforated plate providing a rough surface like e.g. a porous frit made of any inert material like e.g. silica or a polymer; a metal sieve having fine needles on its surface; a perforated plate having sharp edges at the perforation sites; a piercing device having sharp edges or (a) needle(s), sand or any other particulate inert material. In a preferred embodiment a porous frit, serving as liquid-permeable element (4) as well is serving as a component puncturing the barrier material, if said barrier (5) is pressed to the element (4) when an external force as described above is applied to the device.

According to one of the simplest embodiments of the present invention the device can represent a hollow body (1) having at least one open end, containing inside of the hollow body (1) at least one type of a matrix binding, absorbing, adsorbing, chelating or retaining by filtration any contaminant of a biomolecule isolated or purified from a biological sample, whereas the biomolecule of interest is essentially not bound, absorbed, adsorbed or retained and preferably at least one liquid permeable element (4). Preferably the hollow body comprises further at least one barrier (5).

If the hollow body (1) comprises a liquid permeable element (4) as well as a barrier (5) it is possible that at least one of the liquid permeable element(s) (4) can be adjacent to at least one of the barrier(s) (5), wherein "adjacent" means that it is either close to the barrier (5), however, doesn't contact it, or that it is in direct contact with the barrier (5). In case the barrier (5) represents a coating it is preferred that the coating is placed on at least one surface of a liquid-permeable element (4), particularly preferred on one surface of a frit, filter or membrane. In any case the liquid permeable element(s) (4) can be placed above or below of the barrier (5), wherein "above" and "below" is meant in the same sense as described above for the component or material which punctures, cuts or ruptures the barrier material. Preferably the barrier (5) is above the liquid-permeable element (4), which means, that said barrier (5) is adjacent to the upper surface of a liquid-permeable element (4), if the device is positioned in the use mode (inlet (2) up, outlet (3) down).

According to the invention the hollow body (1) may contain more than one of the liquid permeable elements (4) and/or barriers (5), wherein the elements (4) or barriers (5) are separating the hollow body (1) into several compartments. The hollow body may comprise as well 3, 4, 5, 6 or more of the liquid permeable elements (4) or barriers (5), dependent from the intended use of the device.

If more than one barrier (5) is contained in the hollow body (5) it is preferred that they have different resistance against external forces before they become liquid permeable. In particular it is preferred that several barriers contained inside of the same hollow body (1) show from the inlet (2) to the outlet (3) side an increased resistance against the same type of external force. For example if three barriers (5) are contained in the hollow body (1) the first barrier (5) (which is the closest to the inlet side) has a defined resistance against centrifugal forces. The second barrier (5) (which is more inside of the hollow body) has an increased resistance against centrifugal forces compared to the first barrier and accordingly centrifugation has to be accelerated to make the second barrier liquid permeable. The third barrier (5) (which is farthest from the inlet side of the hollow body) has again an increased resistance against centrifugal forces compared to the second barrier and accordingly centrifugation has to be accelerated to make the third barrier liquid permeable. Each of the barriers (5) can be independently selected from the materials described above for the barrier, but it is preferred that they either consist of different materials or of the same basic material, but showing different properties. For instance each of the barriers may consist of the same thermoplastic polymer film, however each of the films has a different thickness. A further possibility is that the barriers (5) are differently treated, e.g. the first barrier comprises an orifice which opens by application of a centrifugal force, the second barrier is a film of a defined thickness having a tinned area serving as a predetermined breaking point and the third barrier is a film of the same material having a continuous thickness becoming porous when the centrifugal force is increased so that said film is contacted with a rough surface of a porous material, e.g. a frit placed adjacent below said third barrier. Another principle is that the foil is as thin, that the foil becomes permeable because of the pressure due to static head of the liquid, if an external force like e.g. centrifugation is applied.

The embodiments exemplified here are not limiting the possible embodiments. It is clear for a skilled person that any combination of barrier materials and/or material treatments can be used as long as the barriers (5) contained in the hollow body (1) of the device allow a compartmentation of said hollow body (1) and can be made liquid permeable by applying any external force. Preferably the barriers (5) can be made sequentially liquid permeable, wherein "sequentially" means that they become liquid permeable one after the other by increasing the external force or by changing the external force.

Particularly preferred the device comprises (i) at least one hollow body, each hollow body (1) having an inlet (2) and an outlet (3); (ii) at least one type of solid or gelly material binding, adsorbing, absorbing, chelating or retaining compounds contaminating any desired biomolecule, but essentially not the biomolecule; (iii) at least one liquid permeable element (4) like preferably a porous frit, filter, fleece, a fiber matrix or membrane, placed above the outlet (3); (iv) optionally at least one removable closing device (6) to seal the inlet (2) and/or outlet (3) of the hollow body; (v) optionally at least one barrier (5) placed above the outlet (3) or adjacent to at least one of the liquid permeable element(s) (4); and (vi) optionally at least one collection tube to collect a mobile phase (eluate) after having passed the outlet (3).

Preferably at least one liquid permeable element (4) is in proximate neighborhood to the outlet side of the device. "Proximate" means that no further reaction compartment of the hollow body is between the element (4) and the outlet, however, due to the construction of the device indeed some space might be between the element (4) and the end of the device.

A further embodiment wherein the preferred properties are achieved is a device comprising several hollow bodies (1) as described above, wherein either each of the hollow bodies (1) are build up similarly or the assembly of the hollow bodies differ from each other, however, at least a part of the hollow bodies fall under the description as defined above.

Although the form of the device is not limiting the present invention, in a preferred embodiment the hollow body/bodies of the device is/are at least partially cylindrical or at least partially conical. Non-limiting examples for embodiments of the invention are reaction tubes, reaction cups, collection tubes, collection containers, a column body, centrifugation tubes, microcentrifuge tubes, in particular compartmented containers like tubes, cups, flasks, chromatographic columns, spin columns, plastic syringe, multi well plates, multiwell blocks, multiwell column plates, flasks, bottles, cups, phiols, collection or centrifugation vessels or similar.

The device can further comprise a removable closing device (6) on at least one of the open ends. Said closing device serves to keep the inside of the device clean and/or sterile or optionally to keep the content of the device inside of the hollow body (1). The closing device (6) can be easily removed before, during and/or after usage of the device. Preferably the closing device (6) is used when the device contains any liquid or a flowable or movable solid material. The closing device (6) can be for example a cap, a plug, a cover plate, a film or foil, or any other suitable removable closing device. It can be reclosable or a disposable closing device. The closing devices (6) of an inlet (2) and an outlet (3) side can differ from each other or can be the same type of closing device (6).

The device of the present invention can be used for the treatment of a sample, particularly of a liquid containing sample. With "liquid sample" is meant that either the sample itself is a liquid, solution, suspension or dispersion, or any gelly, solid or particulate sample or a biological sample as described above is combined with any liquid or solution to obtain a solution, dispersion or suspension. Preferably the device can be used for the treatment of at least one liquid sample comprising any biomolecule, e.g. for isolation or purification of at least one biomolecule from said sample. The liquid can be (temporally) retained in at least one of the compartments of the device and can be moved sequentially from one compartment to the next or can be released, respectively, at desired time points by applying respectively an (optionally increasing) external force to the device as described above.

Furthermore the device according to the present invention can be used for separating a multiphase liquid system or a multiphase liquid/solid system.

The present invention comprises further a method for isolation or purification of at least one biomolecule of interest from a sample comprising at least one type of biomolecules, comprising (a) placing the sample inside of a hollow body (1) of a device as described above comprising at least one solid or gelly matrix binding, absorbing, adsorbing, chelating or retaining by filtration any contaminant of the biomolecule of interest, but essentially not the biomolecule, wherein either the sample is a liquid sample, or the sample is contacted with any liquid before or after placing the sample inside of the hollow body, or the hollow body comprises a liquid coming in contact with the sample when said sample is placed into the device, (b) optionally incubating the sample inside of the hollow body (1), (c) applying an external force, preferably pressure, drag force or driving power to the device, resulting in that the biomolecule of interest is transferred to a next compartment or to the outlet (3) of the hollow body (1), (d) collecting an eluate comprising the biomolecule of interest.

Any pretreatment is possible, e.g. lysis may be carried out in another device before the lysate is placed to the purification column.

In the method according to the invention the hollow body (1) of the device comprises a solid or gelly matrix material as defined above. Additionally in the hollow body (1) any liquid or solution can be contained, like a lysis buffer for cell lysis, a liquid for tissue dissolution, enzyme containing solutions, an organic solvent or any other liquid or solution commonly used during isolation and/or purification of a biomolecule from a sample. The hollow body may comprise several compartments which may be at least partially filled with different types of matrix materials as defined above, liquids, buffers or solutions or mixtures thereof.

In step (a) the sample comprising at least one biomolecule of interest is placed into the hollow body, e.g. a first compartment of the hollow body (1) of the inventive device. Said sample is either a liquid sample, or the sample is a solid sample like a cell, tissue or any other of the biological samples mentioned above containing less liquid and is contacted with any liquid before or after placing the sample inside of the hollow body, or the hollow body comprises a liquid coming in contact with the sample when said sample is placed into the device.

The method comprises at least one optional incubation step (b) wherein ingredients of the solutions or buffers comprised in the sample are allowed to be active or to react with the biological sample. For example, if the biological sample is a cell containing or tissue containing sample and a lysis buffer was added to said sample, the lysis of the cells or tissue is allowed to occur during an optional incubation step. On the other hand, during (an) incubation step(s) any binding, chelating, absorption or adsorption of sample contaminants to the solid matrix material contained in the hollow body (1), may occur.

In step (c) an external force is applied to the device, resulting in a transfer of at least a part of the liquid part of the sample into a next compartment of the hollow body (1) or to the outlet (3) of the hollow body (1), respectively. Preferably each of the compartments comprising a solid or gelly matrix is bordered by a liquid permeable element (4) and therefore by the external force the liquid sample part is transferred through said liquid permeable element (4) whereas the solid or gelly matrix material charged with the contaminants remains in the compartment beyond the liquid permeable element (4). In an embodiment wherein the hollow body (1) comprises several different matrix materials, e.g. in different compartments, it is possible that said compartments are only separated by the liquid permeable element(s) (4) or that the compartments are separated by a barrier (5) or by both. However, an embodiment where several different matrix materials are contained in a hollow body without any compartmentation, e.g. by only mixing said matrix materials or by layering the material one on top of the other inside of the hollow body (1) as well is comprised in the scope of the present invention. However, it is in any case preferred that proximate to the outlet side of the hollow body (1) at least one liquid permeable element (4) is contained to retain any solid or gelly material inside of the hollow body (1) when the liquid sample part comprising the biomolecule of interest is leaving the hollow body (1).

If the device of the present invention comprises at least one barrier (5) it is preferred that a defined first external force is applied to the first barrier (5), resulting in that said first barrier (5) becomes liquid permeable. If further barriers (5) are contained in the hollow body (1) it is particularly preferred that only the first barrier (5) (the closest to the inlet side (2)) becomes liquid permeable during application of a first defined external force in step (c). E.g. pressure may be applied to the inlet (2) of the device, pressing the biomolecule of interest into a next compartment of the hollow body (1); or centrifugal forces are applied to the device transferring al least a part of the liquid comprising the biomolecule of interest into a next compartment of the hollow body (1); or a combination of said forces is applied to the device. In case that only one barrier (5) is contained or remained in the hollow body it is as well possible to apply vacuum to the outlet (3) of the device, sucking the biomolecule of interest to the outlet side of the device.

If several barriers (5) are contained in the device incubation according to step (b) and application of an external force according to step (c) may be repeated, wherein a further external force is applied to the device, e.g. an increased pressure or centrifugal force, wherein it is preferred that said further external force differs from the first external force applied in step (c), either a different type of force may be applied or the intensity of the force changes. The application of the additional external force renders the next present barrier liquid permeable and the liquid sample part is transferred either in a next compartment of the hollow body (1) or is eluted from the device. In case that the sample is transferred into a next compartment optionally steps (b) and (c) independently may be repeated as often as necessary to overcome all barriers (5) inside of the hollow body (1), wherein preferably each following barrier (5) is more resistant against an external force than the barrier (5) before and accordingly in any further step the applied external force is increased or the type of the applied external is changed.

Each of the compartments might be at least partially filled with any liquid or any solid material suitably used during any treatment of a biological sample, wherein according to the invention at least one of the compartments comprises a solid or gelly matrix material binding, absorbing, adsorbing, chelating or retaining by filtration any contaminant of a biomolecule of interest, however, essentially not said biomolecule.

Comprised in the present inventive method is an embodiment wherein the hollow body (1) of the device comprises 2, 3, 4, 5 or 6 liquid permeable elements (4) or barriers (5), resulting in 3, 4, 5, 6 or 7 compartments of the hollow body (1), therefore steps (b) and/or (c) may be repeated as often as necessary during an isolation or purification process to overcome all the contained barriers (5) and to obtain in step (d) an eluate containing the biomolecule of interest.

As well comprised in the method of the invention is that during the process comprising steps (a) to (d) at any stage additionally any further step is carried out. For example at any stage any additional liquid might be added into the hollow body (1) of the device, e.g. by pipetting the liquid into the hollow body (1) from the inlet (2) side. Furthermore any heating or cooling step may be carried out if appropriate for the intended result. Additionally or alternatively steps for mixing like inverting or shaking might be useful for the intended result.

In a last step (d) at least one eluate passing the last compartment is collected. Independent from any further optional steps between step (b) and step (d) the biomolecule of interest can be obtained after applying at least once an external force to the inventive device.

Dependent from the used isolation or purification procedure and the matrix or matrices contained in the hollow body (1) of the device the biomolecule of interest may be contained in the first eluate passing the liquid-permeable element (4), or the biomolecule of interest is contained in any later eluate. For example, if the matrix in the last compartment before the outlet (3) is a binding, absorbing or adsorbing matrix for the biomolecule and any washing steps are comprised in the isolation/purification procedure, the interesting biomolecule is comprised in a later eluate. In this case said eluate either can be obtained by applying again any external force to the device, or the eluate is able to pass the liquid-permeable element by gravitational force only. According to the invention at least one matrix contained in the hollow body (1) is essentially not absorbing, adsorbing or binding the biomolecule of interest.

The device of the present invention can be prepared by placing at least one liquid permeable element (4) inside of a hollow body (1) having at least one open end, wherein at least one element (4) is preferably proximate to one open end of the hollow body (1). The element(s) (4) is/are placed in the hollow body (1) in a way that the element (4) or each of the elements (4) is either in direct contact with all of the inner side walls of the hollow body (1) and flushes with said side walls, or the element(s) is/are placed in a holder (7) which is in contact with all of the inner side walls of the hollow body (1) and flushes with said side walls. Any remaining gap between the element(s) (4) and the side walls or the holder (7) and the side walls might be filled with an adhesive or sealing material.

Additionally to the element(s) (4) at least one barrier (5) may be placed inside of the hollow body (1), either adjacent to at least one element (4) or spaced apart of it/them. The liquid-permeable element (4) either can be placed inside of the hollow body (1) before the barrier (5) is placed inside, or the barrier (5) is placed inside the hollow body (1) before the liquid-permeable element (4) is placed inside the body (1). In one possible preparation method of the device at least one liquid-permeable element (4) is brought in contact with at least one barrier (5) material and thereafter the combined "module" of liquid-permeable element (4) and barrier (5) is placed inside of the hollow body. For instance such a "module" can comprise one liquid-permeable element (4), preferably a frit, fleece, a fiber matrix, filter or membrane and one barrier (5) material, preferably a film, foil or coating, membrane, septum, hydrophobic sintered material or hydrophobic fibrous material, or it can comprise two liquid-permeable elements (4), wherein between them two at least one barrier (5) material is contained like a "sandwich" structure. The hollow body (1) can comprise one or several of such modules, and optionally additionally at least one separate barrier (5) or liquid-permeable element (4). It is particularly preferred that if at least one compartment of the hollow body comprises a solid matrix said compartment is bordered by at least one liquid permeable element (4) or a module comprising at least one liquid permeable element and at least one barrier (5) to retain the solid matrix in the compartment when the liquid part is transferred into the next compartment or to the outlet (3).

It is preferred that the barrier (5) and/or the liquid-permeable element (4) or the module comprising both are either sized in a way that thy fit exactly into the hollow body, flushing with all of the side walls of said hollow body, or that they are placed in or connected with a holder (7) which fits exactly into the hollow body, flushing with all of the side walls of said hollow body. Any remaining gap might be filled with an adhesive or sealing material. The barrier (5) and the optional liquid-permeable element (4) can be fixed at the predetermined point by using a clamping ring or grid below the barrier (5) and/or the optional liquid-permeable element (4).

If no holder (7) is used, it is either preferred that the hollow body comprises at least one flange or support element for any of the liquid-permeable element(s) (4) or the barrier(s) (5) or both whereon the element (4) or the barrier (5) can bear, or the barrier (5) or element (4) are placed upon a support element which is transfixed inside the hollow body (1) or the barrier (5) can bear, or the barrier (5) and/or the liquid-permeable element (4) is contacted with the side walls via a suitable adhesive like e.g. a silicon adhesive, a cross-linking resin, a gum, a thermoplastic or thermosetting polymer. The type of adhesive is not limiting the invention as long as it is not reactive with one of the ingredients added into the inventive device if used as intended. In a further embodiment the hollow body (1) is conical and the liquid-permeable element (4) and/or the barrier (5) are sized in a way that they fit only at a predetermined place inside of the hollow body (1) and are placed at this predetermined place by pressing the element (4) or the barrier (5) on said place where they are kept by tension. In any of the embodiments it might be advantageous to seal any remaining gap between the liquid-permeable element (4) and/or the barrier (5) or the holder (7) with a suitable sealing material. Suitable sealing materials are e.g. silicone polymers, thermoplastic or thermosetting polymers or resins.

Optionally the hollow body (1) can be charged additionally with (a) component(s) or material(s) which punctures, cuts or ruptures the barrier material, if this obtainable effect is not already provided by e.g. the liquid-permeable element (4).

After placing at least one liquid permeable element (4) inside of the hollow body (1) said hollow body or at least one compartment of the hollow body (1) is at least partially filled with a solid or gelly matrix binding, absorbing, adsorbing, chelating or retaining by filtration at least one type of contaminant of a desired biomolecule, but essentially not said biomolecule. Before or after said step of addition of said matrix the hollow body might be filled additionally with any other compound, liquid, solution, buffer or matrix suitable for any desired purification or isolation process. This means according to a desired process protocol the hollow body might be sequentially filled with any suitable solid, gelly or liquid compound or solution, in particular in a sequence allowing a suitable purification or isolation of a desired biomolecule. Dependent from the purification or isolation protocol the ingredients of the matrices or solutions filled in any compartment(s) can vary, however, according to the invention at least one compartment is filled with a matrix binding, absorbing, adsorbing, chelating or retaining by filtration at least one type of contaminant of a desired biomolecule, but essentially not said biomolecule. For example, if it is desired any other compartment can be filled with a lysis buffer for cell or tissue lysis, with any matrix specifically binding the biomolecule of interest for further purification or with a reaction buffer allowing any reaction of the biomolecule of interest. Preferably the device comprises in the hollow body more than one compartment at least partially filled with a solid or gelly matrix binding, absorbing, adsorbing or chelating contaminating compounds, e.g. two, three, four or more different compartments with two, three, four or e more different types of such solid or gelly matrices, wherein each of said matrices binds, absorbes, adsorbes or chelates a different type of a contaminating compound.

If presently a hollow body having "compartments" is described as well a hollow body is meant having only one compartment, filled with said matrix or matrices. Preferred matrices are for example Chelex resin, silicate particles or fibers, ion exchanging materials or any similar. In a particularly preferred embodiment at least one compartment of the hollow body is at least partially filled with a chelating resin, not binding the biomolecule of interest, e.g. Chelex resin for nucleic acid isolation.

If further solid or gelly compounds, liquids or solutions are filled into the hollow body (1) it is preferred, however not necessary that either at least one liquid permeable element (4) or at least one barrier (5) or both is placed into the hollow body (1) before the next compound or solution is added. Accordingly in a preferred embodiment the hollow body is compartmented by at least one further element (4) or at least one barrier (5), if it contains different types of solid or gelly matrices and/or liquids or solutions, but this is not mandatory.

A further possibility according to the invention is a method wherein the biological sample comprising a biomolecule of interest is first contacted outside of an inventive device with at least one matrix binding, absorbing, adsorbing, chelating or retaining by filtration at least one type of contaminant of the desired biomolecule, but essentially not said biomolecule. After contacting the matrix with said sample and optionally any additional treatment step(s) the whole sample comprising the matrix can be transferred into a device having a hollow body (1) and inside of the hollow body (1) at least one liquid permeable element (4). After the transfer of the sample including the matrix into said device an external force as described above can be applied to the device resulting in elution of at least a part of the liquid part of the sample containing the biomolecule(s) of interest.

The present invention further includes a kit for treating a biological sample or for purification or isolation of a biomolecule from a biological sample, comprising a device as described above. Alternatively the kit comprises a device having at least one hollow body (1) having at least one open end and inside of the hollow body (1) at least one liquid permeable element (4) and separated therefrom at least one further container comprising a solid or gelly matrix binding, absorbing, adsorbing, chelating or retaining by filtration at least one type of contaminant of a desired biomolecule, but essentially not said biomolecule.

The invention claimed is:
1. A device, comprising:
(i) at least one hollow body, each hollow body having an inlet and an outlet, wherein when the device is positioned in use mode, the inlet is an opening at the upper end of the hollow body, and the outlet is an opening at the bottom side of the hollow body;
(ii) inside of the hollow body, one or more type(s) of solid or gelly matrix material(s) binding, adsorbing, absorbing, chelating or retaining compounds contaminating a desired biomolecule, wherein at least one type of the solid or gelly matrix material(s) is selected from the group consisting of a chelating resin, a cationic or anionic ion exchanging matrix material, a matrix comprising specific binding sites for undesired compounds, silica, polysaccharides or derivatives thereof, hydropohobic interaction chromatography (HIC) particles, size exclusion materials, gel filtration material, minerals, iminodiacetic acid (IDA), IDA derivatives, nitrilo acetic acid (NTA), NTA derivatives, a resin or other substrate with IDA or NTA groups or derivatives thereof, EDTA, amphipol, charcoal, polyvinylpyrrolidone (PVP), superabsorbing polymers, and non-fat milk cocktails;
(iii) one or more porous liquid-permeable element(s) inside of the hollow body, wherein at least one of the porous liquid-permeable element(s) is below at least one type(s) of the matrix material(s) of (ii);
(iv) optionally one or more removable closing device(s) to seal the inlet or outlet of the hollow body or both the inlet and outlet of the hollow body; and
(v) inside of the hollow body, one or more barrier(s) that are non-permeable for liquids and solids under ambience conditions, but become irreversibly liquid-permeable by applying an external force to said barrier, wherein at least one of the barrier(s) is in contact with all of the inner side walls of the hollow body and flushes with the side walls or is placed in a holder that flushes with the side walls, wherein at least one of the barrier(s) of (v) is between at least one type of the matrix material(s) of (ii) and at least one of the porous liquid-permeable element(s) of (iii), and wherein the at least one of the porous liquid-permeable element(s) is capable of rendering the at least one of the barrier(s) irreversibly liquid-permeable when applying an external force to said barrier so that said barrier is pressed to said porous liquid-permeable element and becomes broken, punctured, cut or ruptured.
2. The device of claim 1, wherein the at least one of the porous liquid-permeable element(s) is a porous frit, filter, fleece, fiber matrix, or membrane.
3. The device of claim 1, wherein at least one type of the solid or gelly matrix material(s) is in form of powder, particles, beads, granules, spheres, a fleece, or at least one membrane.
4. The device of claim 1, wherein the polysaccharide comprises chitosane, starch, glycogen, or cellulose.

5. The device of claim 1, wherein the liquid-permeability is irreversible by breaking, puncturing, rupturing or cutting the barrier.
6. The device of claim 1, wherein the hollow body is at least partially cylindrical or conical.
7. The device of claim 6, wherein the device is a reaction tube, a reaction cup, a collection tube, a collection container, a column body, a spin column, a centrifugation tube, a microcentrifuge tube, or a compartmented container.
8. The device of claim 7, wherein the compartmented container is a tube, cup, flask, chromatographic column, spin column, plastic syringe, multiwell plate, multiwell block, multiwell column plate, bottle, phiol, collection vessel, or centrifugation vessel.
9. A method for preparing a device of claim 1, comprising:
placing one or more porous liquid-permeable element(s) and one or more barrier(s) inside a hollow body having an inlet and an outlet, wherein at least one of the barrier(s) is placed above at least one of the liquid-permeable element(s), and is non-permeable for liquids and solids under ambience conditions, but becomes liquid-permeable by applying an external force to said barrier so that said barrier is pressed to said liquid-permeable element and becomes broken, punctured, cut or ruptured; and
filling the hollow body at least partially with one or more type(s) of solid or gelly matrix material(s) binding, adsorbing, absorbing, chelating or retaining compounds contaminating a desired biomolecule, but essentially not the desired biomolecule, wherein at least one type of the solid or gelly matrix material(s) is selected from the group consisting of a chelating resin, a cationic or anionic ion exchanging matrix material, a matrix comprising specific binding sites for undesired compounds, silica, polysaccharides, hydropohobic interaction chromatography (HIC) particles, size exclusion materials, gel filtration material, minerals, iminodiacetic acid (IDA), IDA derivatives, nitrilo acetic acid (NTA), NTA derivatives, a resin or other substrate with IDA or NTA groups or derivates thereof, EDTA, specific antibodies, amphipol, charcoal, polyvinylpyrrolidone (PVP), superabsorbing polymers, and non-fat milk cocktails.
10. The method of claim 9, wherein at least one of the porous liquid-permeable element(s) is placed proximate to the outlet of the hollow body.
11. The method of claim 10, wherein at least one of the liquid-permeable element(s) is placed inside the hollow body in a way that said element fits exactly into the hollow body, flushing with all of the side walls of said hollow body, or is placed in a holder that fits exactly into the hollow body, flushing with all of the side walls of said hollow body, wherein any remaining gap is filled with a sealing material.
12. A method for isolation or purification of a biomolecule of interest from a biological sample, comprising
(a) placing the biological sample inside a hollow body of a device of claim 1, wherein
(i) the one or more type(s) of solid or gelly matrix(s) bind, absorb, adsorb, chelate or retain by filtration essentially no biomolecule of interest, and
(ii) either the sample is a liquid sample, or the sample is contacted with a liquid before or after placing the sample inside of the hollow body, or the hollow body comprises a liquid coming in contact with the sample when said sample is placed into the device,
(b) optionally incubating the sample inside of the hollow body, (c) applying an external force to the device, resulting in that the biomolecule of interest is transferred to a next compartment or to the outlet of the hollow body, and (d) collecting an eluate comprising the biomolecule of interest.

13. The method of claim 12, wherein the external force is pressure, drag force, or driving power.

14. The method of claim 13, wherein the hollow body of the device comprises 2, 3, 4, 5 or 6 liquid-permeable elements or barriers, resulting in 3, 4, 5, 6 or 7 compartments of the hollow body, optionally comprising different types of solid or gelly matrix materials binding, absorbing, adsorbing or chelating contaminants of the biomolecule of interest, but essentially not said biomolecule and/or any liquid, solution or buffer, and steps (b) and/or (c) are repeated as often as necessary during an isolation or purification process to overcome all the contained elements or barriers and to obtain an eluate containing the biomolecule of interest.

15. The method of claim 14, wherein at least one of the compartments of the hollow body of the device comprises a further solid matrix and/or at least one liquid before the biomolecule comprising sample is added.

16. A method for isolation or purification of a biomolecule of interest from a biological sample, comprising (a) contacting the biological sample with at least one solid or gelly matrix material binding, absorbing, adsorbing, chelating or retaining by filtration at least one type of contaminant of the biomolecule of interest, but essentially not said biomolecule, wherein at least one type of the solid or gelly matrix material(s) is selected from the group consisting of a chelating resin, a cationic or anionic ion exchanging matrix material, a matrix comprising specific binding sites for undesired compounds, silica, polysaccharides, hydropohobic interaction chromatography (HIC) particles, size exclusion materials, gel filtration material, minerals, iminodiacetic acid (IDA), IDA derivatives, nitrilo acetic acid (NTA), NTA derivatives, a resin or other substrate with IDA or NTA groups or derivatives thereof, EDTA, specific antibodies, amphipol, charcoal, polyvinylpyrrolidone (PVP), superabsorbing polymers, and non-fat milk cocktails, (b) thereafter transferring the whole sample comprising the matrix into a device, wherein the device has (i) a hollow body that has an inlet and an outlet, and (ii) one or more liquid-permeable element and one or more barrier(s) inside the hollow body, wherein at least one of the barrier(s) is placed above at least one of the liquid-permeable element(s) and is non-permeable for liquids and solids under ambience conditions, but becomes liquid-permeable by applying an external force to said barrier so that said barrier is pressed to said porous liquid-permeable element and becomes broken, punctured, cut or ruptured, and wherein the at least one barrier is in contact with all of the inner side walls of the hollow body and flushes with the side walls or is placed in a holder that flushes with the side walls, (c) applying an external force to the device, resulting in that the biomolecule of interest is transferred to a next compartment or to the outlet of the hollow body, and (d) collecting an eluate comprising the biomolecule of interest.

17. The method of claim 16, wherein the external force of step (c) is pressure, drag force or driving power.

18. A kit for treating a biological sample or for purification and/or isolation of a biomolecule from a biological sample, comprising (i) a device of claim 1, or (ii) (a) a device that comprises a hollow body and therein one or more liquid-permeable element(s) and one or more barrier(s), wherein at least one of the barrier(s) is placed above at least one of the liquid-permeable element(s), and is non-permeable for liquids and solids under ambience conditions, but becomes liquid-permeable by applying an external force to said barrier so that said barrier is pressed to said porous liquid-permeable element and becomes broken, punctured, cut or ruptured, wherein the at least one barrier is in contact with all of the inner side walls of the hollow body and flushes with the side walls or is placed in a holder that flushes with the side walls, and (b) in a further container, a solid or gelly matrix material binding, absorbing, adsorbing, chelating or retaining by filtration at least one type of contaminant of a biomolecule of interest, but essentially not said biomolecule, wherein the solid or gelly matrix material is selected from the group consisting of a chelating resin, a cationic or anionic ion exchanging matrix material, a matrix comprising specific binding sites for undesired compounds, silica, polysaccharides, hydropohobic interaction chromatography (HIC) particles, size exclusion materials, gel filtration material, minerals, iminodiacetic acid (IDA), IDA derivatives, nitrilo acetic acid (NTA), NTA derivatives, a resin or other substrate with IDA or NTA groups or derivatives thereof, EDTA, specific antibodies, amphipol, charcoal, polyvinylpyrrolidone (PVP), superabsorbing polymers, and non-fat milk cocktails, wherein when (a) and (b) are assembled together, the at least one barrier is between the solid or gelly matrix material and the at least one liquid-permeable element.

19. The device of claim 1, wherein at least one of the barrier(s) of (v) is in direct contact with one of the porous liquid-permeable element(s) of (iii).

20. The device of claim 1, wherein at least one of the barrier(s) of (v) is above the matrix material of (ii).

21. The device of claim 1, wherein the device comprises one or more removable closing device(s) to seal the inlet or outlet of the hollow body or both the inlet and outlet of the hollow body.

22. The device of claim 1, further comprising at least one collection tube to collect a mobile phase after having passed the outlet.

* * * * *

UNITED STATES PATENT AND TRADEMARK OFFICE
CERTIFICATE OF CORRECTION

PATENT NO. : 10,514,330 B2
APPLICATION NO. : 13/809563
DATED : December 24, 2019
INVENTOR(S) : Holländer et al.

Page 1 of 1

It is certified that error appears in the above-identified patent and that said Letters Patent is hereby corrected as shown below:

Claim 16, Column 17, Line 45:
"or more liquid-permeable element and one or more" should read --or more liquid-permeable element(s) and one or more--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*